(12) United States Patent
Watanabe

(10) Patent No.: US 8,237,838 B2
(45) Date of Patent: Aug. 7, 2012

(54) IMAGE SENSING APPARATUS AND CONTROL METHOD THEREOF

(75) Inventor: Hajime Watanabe, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 284 days.

(21) Appl. No.: 12/693,546

(22) Filed: Jan. 26, 2010

(65) Prior Publication Data

US 2010/0194900 A1    Aug. 5, 2010

(30) Foreign Application Priority Data

Feb. 3, 2009  (JP) .................................. 2009-022959

(51) Int. Cl.
H04N 5/222 (2006.01)
H04N 5/232 (2006.01)
(52) U.S. Cl. ................................ 348/333.02; 348/211.1
(58) Field of Classification Search ............. 348/333.01, 348/333.02, 333.05, 333.1, 333.12, 211.2, 348/211
See application file for complete search history.

(56) References Cited

U.S. PATENT DOCUMENTS

| | | | |
|---|---|---|---|
| 2007/0019083 A1* | 1/2007 | Nakashima | 348/239 |
| 2007/0201767 A1 | 8/2007 | Fujita | |
| 2008/0186385 A1* | 8/2008 | O | 348/207.99 |
| 2009/0091637 A1* | 4/2009 | Suzuki | 348/222.1 |

FOREIGN PATENT DOCUMENTS

| | | |
|---|---|---|
| JP | 6-259534 | 9/1994 |
| JP | 2007-020104 | 1/2007 |
| JP | 2007-259415 | 10/2007 |

* cited by examiner

Primary Examiner — Tuan Ho
Assistant Examiner — Shahbaz Nazrul
(74) Attorney, Agent, or Firm — Fitzpatrick, Cella, Harper & Scinto

(57) ABSTRACT

An image sensing apparatus that is capable of communicating with an external apparatus, comprising: an image sensing unit configured to sense an object and generate image data; an identification data generation unit configured to generate, from the image data, identification data for identifying a feature of the object; a storage unit configured to store the identification data; a display unit configured to display the image data; a communication unit configured to receive identification data for identifying a feature of an object captured by another image sensing apparatus during communication with the other image sensing apparatus; a determination unit configured to determine the image capture status of each object based on the identification data received by the communication unit; and a control unit configured to control the display unit to identifiably display the image capture status of each object determined by the determination unit.

10 Claims, 11 Drawing Sheets

| FILE NAME | PERSON ID | NUMBER OF PERSONS | FACE REGION |
|---|---|---|---|
| IMG_0001.JPG | 1,2 | 2 | 1(X0,Y0), 2(X1,Y1) |
| IMG_0002.JPG | 1,2,3,4 | 4 | 1(X2,Y2), 2(X3,Y3), 3(X4,Y4), 4(X5,Y5) |
| IMG_0003.JPG | 2,4 | 2 | 2(X6,Y6), 4(X7,Y7) |
| IMG_0004.JPG | 5,6 | 2 | 5(X8,Y8), 6(X9,Y9) |

| PERSON ID | CAPTURING COUNT |
|---|---|
| 1 | 5 |
| 2 | 7 |
| 3 | 3 |
| 4 | 2 |
| 5 | 4 |
| 6 | 5 |

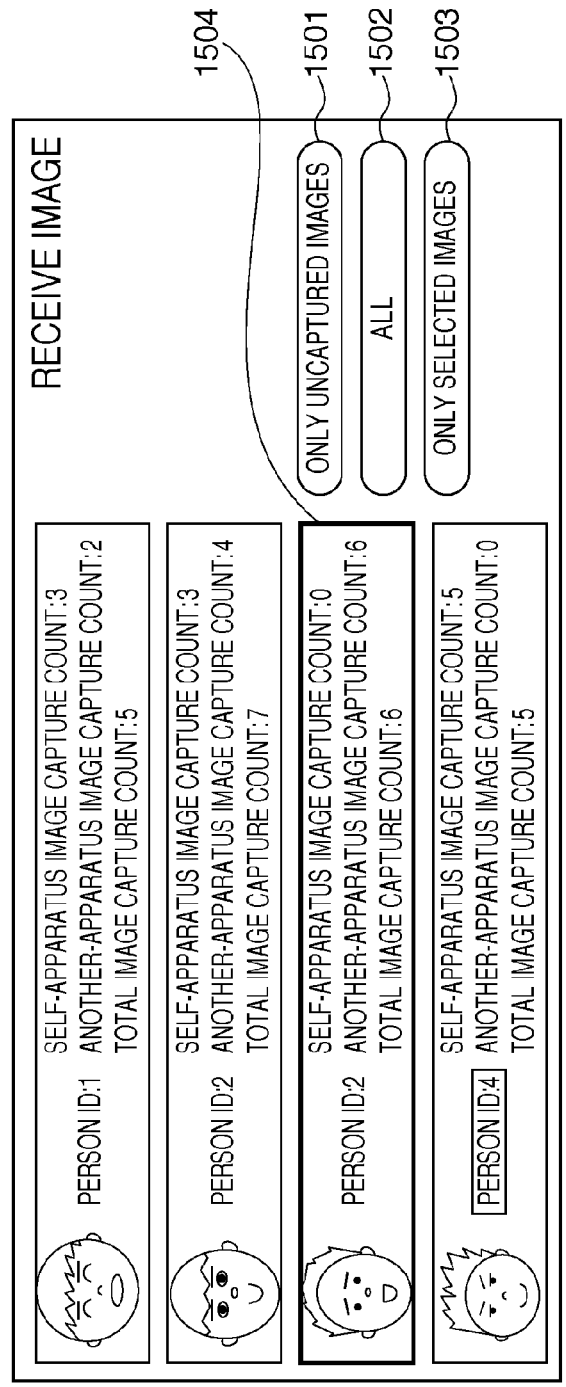

IMAGE SENSING APPARATUS AND CONTROL METHOD THEREOF

BACKGROUND OF THE INVENTION

1. Field of the Invention

The present invention relates to an image sensing apparatus having a communication function with another apparatus and an object recognition function.

2. Description of the Related Art

There has conventionally been proposed a technique of performing face recognition based on data obtained by extracting feature points of a human face from a captured image of an object person, and the degree of coincidence between pre-registered human face recognition data and the feature points (see Japanese Patent Laid-Open No. 6-259534).

There is also known a technique of using face recognition data to search for desired image data from multiple captured images (see Japanese Patent Laid-Open No. 2007-259415).

A technique of managing the image capture count (number of times) for each object by using face recognition data has also been proposed (see Japanese Patent Laid-Open No. 2007-020104).

At an event such as a party or school event, there is a need to equally capture all participants or persons involved in the event as objects. The user takes pictures by taking account of who has been captured, how often he has been captured, and who has not been captured. In practice, however, if there are multiple people, it is difficult to grasp whether all objects have been captured.

According to Japanese Patent Laid-Open No. 2007-020104, the image capture count is displayed in order to notify the user of the image capture status. However, at an event or the like, participants are usually captured by a plurality of users or by one user using a plurality of image capture devices. Thus, the user can grasp only the image capture count of an object for each image capture device, resulting in a high image capture count or the capture of only specific objects.

SUMMARY OF THE INVENTION

In order to solve the aforementioned problems, the present invention provides an electronic device such as an image sensing apparatus that is capable of communicating with an external apparatus, comprising: an image sensing unit configured to sense an object and generate image data; an identification data generation unit configured to generate, from the image data, identification data for identifying a feature of the object; a storage unit configured to store the identification data; a display unit configured to display the image data; a communication unit configured to receive identification data for identifying a feature of an object captured by another image sensing apparatus during communication with the other image sensing apparatus; a determination unit configured to determine the image capture status of each object based on the identification data received by the communication unit; and a control unit configured to control the display unit to identifiably display the image capture status of each object determined by the determination unit.

The present invention also provides a method of controlling an image sensing apparatus that is capable of communicating with an external apparatus, the image sensing apparatus including an image sensing unit configured to sense an object and generate image data, an identification data generation unit configured to generate, from the image data, identification data for identifying a feature of the object, a storage unit configured to store the identification data, and a display unit configured to display the image data, the method comprising the steps of: receiving, via a communication unit, identification data for identifying a feature of an object captured by another image sensing apparatus during communication with the other image sensing apparatus; determining the image capture status of each object based on the identification data received in the receiving step; and controlling the display unit to identifiably display the image capture status of each object determined in the determining step.

According to the present invention, an apparatus accessible to a plurality of storage media including one with a wireless communication function, which can externally transmit data without any cumbersome operation.

Further features of the present invention will become apparent from the following description of exemplary embodiments (with reference to the attached drawings).

BRIEF DESCRIPTION OF THE DRAWINGS

FIG. 14 is a table exemplifying the contents of a person ID management table in the third embodiment; and FIG. 15 is a view exemplifying display of a list of registered persons in the third embodiment.

DESCRIPTION OF THE EMBODIMENTS

Embodiments of the present invention will be described in detail below with reference to the accompanying drawings.

The following embodiments are merely examples for practicing the present invention. The embodiments should be properly modified or changed depending on various conditions and the structure of an apparatus to which the present invention is applied. The present invention should not be limited to the following embodiments.

First Embodiment

Figure 1:
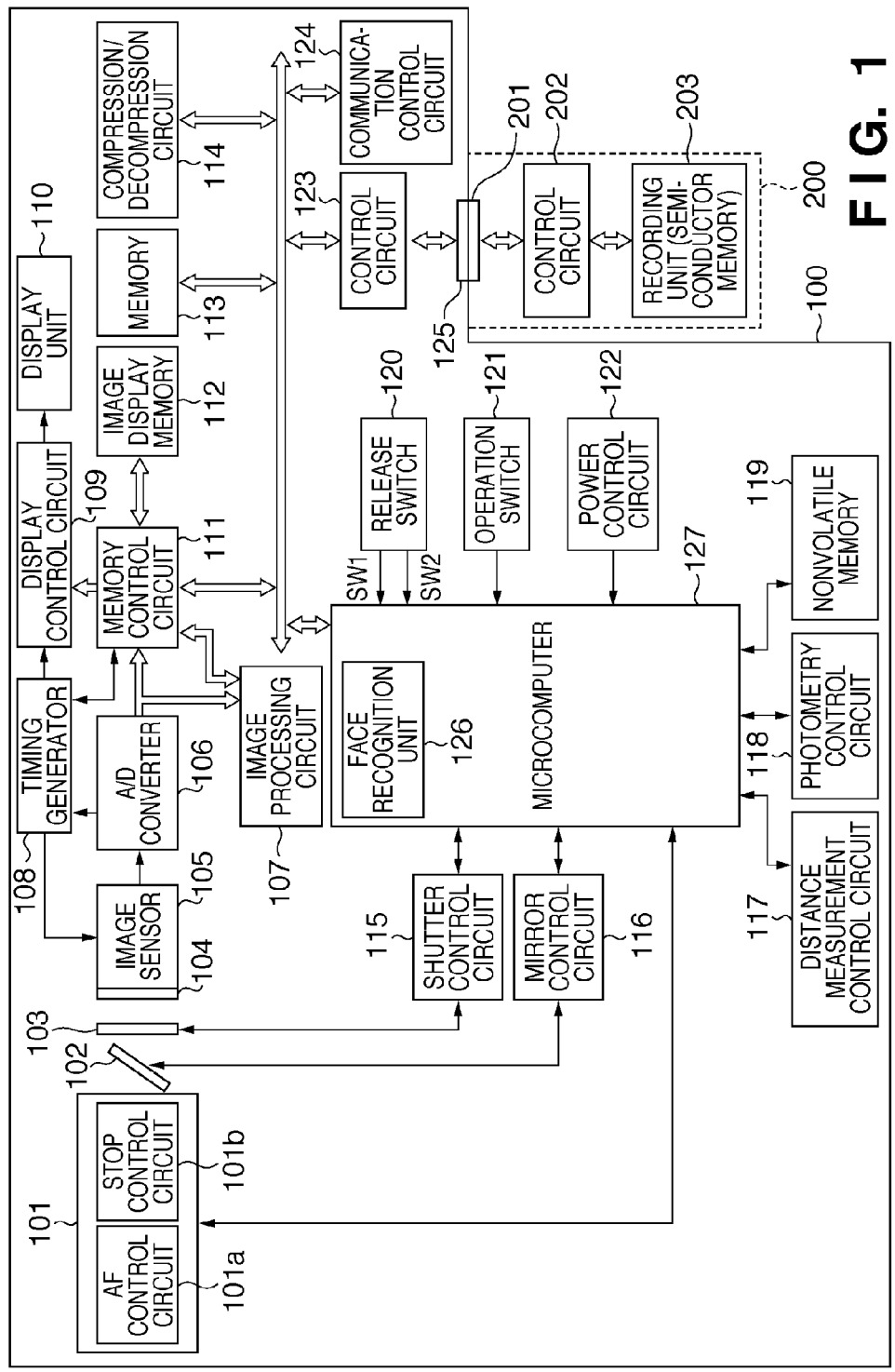
FIG. 1 is a block diagram showing the arrangement of an image sensing apparatus according to the first embodiment of the present invention.

FIG. 1 is a block diagram showing the schematic arrangement of an image sensing apparatus according to the first embodiment of the present invention.

An image sensing apparatus 100 is, e.g., a digital camera. An interchangeable lens unit 101 includes a plurality of lenses. The lens unit 101 communicates with a microcomputer 127 to control an autofocus (AF) control circuit 101a in the lens unit 101, displace a focusing lens in the lens unit 101, and adjust the focus. The displacement amount of the focusing lens is calculated based on output from a distance measurement control circuit 117. The lens unit 101 incorporates a stop control circuit 101b to change an optical aperture value.

A quick return mirror 102 is inserted in the optical path of the image to be captured. The movement of the quick return mirror 102 is controlled between a mirror-down position where it guides object light having passed through the lens unit 101 to a viewfinder optical system (not shown) and a mirror-up position where it retracts from the optical path of the image to be captured. Reference numeral 103 denotes a shutter. An optical filter 104 is covered with dust-proof glass. An image sensor 105 converts the optical image of an object incident via the lens unit 101 into an electrical signal. An A/D converter 106 converts an analog image signal output from the image sensor 105 into a digital signal. An image processing circuit 107 performs predetermined pixel interpolation processing, development processing, and the like for a digital image signal from the A/D converter 106 or image data from a memory control circuit 111, based on processing data added to the image data.

A timing generator 108 supplies clock signals and control signals to the image sensor 105 and A/D converter 106. The memory control circuit 111 and microcomputer 127 (to be described later) control the timing generator 108. The memory control circuit 111 controls the A/D converter 106, the image processing circuit 107, the timing generator 108, an image display memory 112, a memory 113, and a compression/decompression circuit 114.

A digital image signal output from the A/D converter 106 is written in the image display memory 112 or memory 113 via the image processing circuit 107 and memory control circuit 111. A display unit 110 is formed from a TFT LCD or the like. The display unit 110 displays display image data written in the image display memory 112 under the control of a display control circuit 109.

The display unit 110 is mainly arranged on the rear side of the image sensing apparatus. The display unit 110 can also function as an electronic viewfinder by through-displaying a menu window for instructing the user on an operation, the playback image of an image file, or an image obtained by processing image signals sequentially output from the image sensor 105 by the image processing circuit 107. While confirming the framing of an object on the display unit 110, the user can take a picture. Note that sequentially updated through image data are also used for face recognition processing of an object person by a face recognition unit 126 (to be described later).

The memory 113 serves as an image buffer area for temporarily storing captured uncompressed image data. The memory 113 holds processing data used when performing development processing by the image processing circuit 107 for image data, and AF (Auto Focus), AE (Auto Exposure), and WB (White Balance) calculation results. The memory 113 further includes, e.g., a work buffer area for storing data for temporal use, and a file buffer area for storing image data compressed by the compression/decompression circuit 114. The memory 113 has a storage capacity enough to store a predetermined number of still images and a moving image of a predetermined time. Even in continuous shooting to continuously shoot a plurality of still images, many images can be quickly written in the memory 113.

The compression/decompression circuit 114 compresses/decompresses image data into JPEG data by adaptive discrete cosine transform (ADCT) or the like. The compression/decompression circuit 114 reads out image data from the memory 113, compresses/decompresses it, and writes the processed data in the memory 113. A shutter control circuit 115 controls the shutter 103. A mirror control circuit 116 controls the quick return mirror 102 to enter or retract from the optical path of the image to be captured. The distance measurement control circuit 117 measures the distance to an object and controls the focusing lens of the lens unit 101 in accordance with the output. A photometry control circuit 118 measures the brightness of an object and controls the exposure in accordance with the output.

The operation members of the image sensing apparatus 100 will be explained.

The user uses operation members 120 and 121 to input a variety of operation instructions to the microcomputer 127. The operation members 120 and 121 include various button switches, dials, and touch panels.

The release switch 120 includes a switch which is turned on by pressing a release button halfway (SW1). The release switch 120 designates the start of operations to prepare for image capture, such as AF (Auto Focus) processing and AE (Auto Exposure) processing. The release switch 120 further includes a switch which is turned on by pressing the release button fully (SW2). The release switch 120 performs image sensing processing to write a signal read out from the image sensor 105 in the memory 113 via the A/D converter 106 and memory control circuit 111. Then, the image processing circuit 107 executes white balance correction processing and development processing corresponding to a white balance mode set for image data. The image data having undergone development processing is read out from the memory 113 and compressed by the compression/decompression circuit 114.

Subsequently, the start of a series of processes in recording processing is designated to write image data in a recording medium 200. The operation switch 121 is formed from a combination of a menu key, set key, four-way selector key, and playback key (none are shown). While checking a window displayed on the display unit 110, the user can use the operation switch 121 to execute various kinds of operations such as selecting changes in various settings (e.g., the camera's image capturing conditions and development conditions) and designating the playback of an image file.

The microcomputer 127 controls the whole image sensing apparatus 100.

A nonvolatile memory 119 stores a variety of programs such as a program for performing image sensing processing, a program for performing image processing, and a program for recording created image file data on a recording medium. In addition, the memory 119 stores various programs such as an OS which implements and executes multitasking of these programs, and adjustment values for performing various control operations.

The microcomputer 127 includes the face recognition unit 126. The microcomputer 127 extracts a feature region from image data recorded on the recording medium 200 or through image data displayed on the display monitor, and generates identification data for identifying an object person (identification data generation unit). The microcomputer 127 also has the function of recording identification data generated during an image capture operation in memory 113, nonvolatile memory 119, or recording medium 200 to be described later.

Building components and accessory members connected to the image sensing apparatus 100 will be explained.

The power control circuit 122 includes a battery detection circuit, a DC-DC converter, and a switching circuit for switching a block to be energized. The power control circuit 122 detects mounting/dismounting of a battery, the type of battery, and the remaining battery level. Based on the remaining battery level detection result and an instruction from the microcomputer 127, the power control circuit 122 controls the DC-DC converter to supply necessary voltages to respective units including a recording medium for necessary periods.

The control circuit 123 controls a recording medium such as a memory card. The connector 125 connects the recording medium 200 such as a memory card. The communication control circuit 124 controls a wireless or wired communication unit and can communicate with another image capture device and a communication device. The image sensing apparatus in the first embodiment is connected to another image capture device by wireless communication such as a wireless LAN, infrared communication, or Bluetooth.

The recording medium 200 is, e.g., a memory card or hard disk. The recording medium 200 is assumed to be a memory card formed from semiconductor memory. The recording medium 200 comprises a connector 201 which connects the recording medium 200 to the image sensing apparatus 100, a control circuit 202 which interfaces the image sensing apparatus 100 and controls a recording unit 203, and the recording unit 203 formed from a semiconductor memory. The housing of the image sensing apparatus 100 has a slot for receiving the recording medium 200 such as a memory card. The housing contains the entire card, and has an openable lid (not shown) for covering the slot.

The image sensing apparatus 100 (to be also referred to as a self-apparatus) is communicably connected to another image sensing apparatus (to be also referred to as another apparatus) and has a function of receiving identification data generated by another apparatus to identify a person. Another apparatus also has a function of extracting a feature region from image data captured by the apparatus and generating identification data for identifying an object person. Identification data received from another apparatus is used as identification data for identifying a person by the face recognition unit 126, as well as identification data generated by the self-apparatus. Identification data received from another apparatus may be recorded on the recording medium 200, similar to the identification data of the self-apparatus as described above. In the first embodiment, identification data received by another apparatus is assumed to be recorded on the recording medium 200 together with identification data generated by the self-apparatus.

Various methods are known as an object face recognition technique. As an example of this method, a face region is extracted from image data. Identification data is analyzed from the sizes of respective parts obtained from the feature points of physical shapes such as the eyes, nose, mouth, and face contour, and the positional relationship between the parts. By using the identification data, a person is characterized.

The face recognition unit 126 in the first embodiment extracts a person image from image data such as a captured image or through image processed by the image processing circuit 107. According to the above-mentioned method, the feature points of physical shapes such as the eyes, nose, mouth, and face contour are analyzed. The face recognition unit 126 uses the analysis results as identification data (to be referred to as registered self-apparatus identification data) recorded on the recording medium 200 to determine whether the analyzed person image matches identification data (to be referred to as registered another-apparatus identification data) received from another apparatus. From this, the image capture status of each person can be recognized.

In accordance with the analysis result by the face recognition unit 126, the image sensing apparatus 100 is controlled to superimpose and display information about a person on, e.g., an image file played back on the display unit 110. An analysis result upon the capture of the image is stored as new self-apparatus identification data in the recording medium 200, and then is used as self-apparatus identification data, details of which will be described later.

The following description assumes that the image sensing apparatus 100 is configured in advance to be communicable with another apparatus and an image capture mode in which identification data generated by the face recognition unit 126 is used is set.

<Image Capture Processing>

Figure 2:
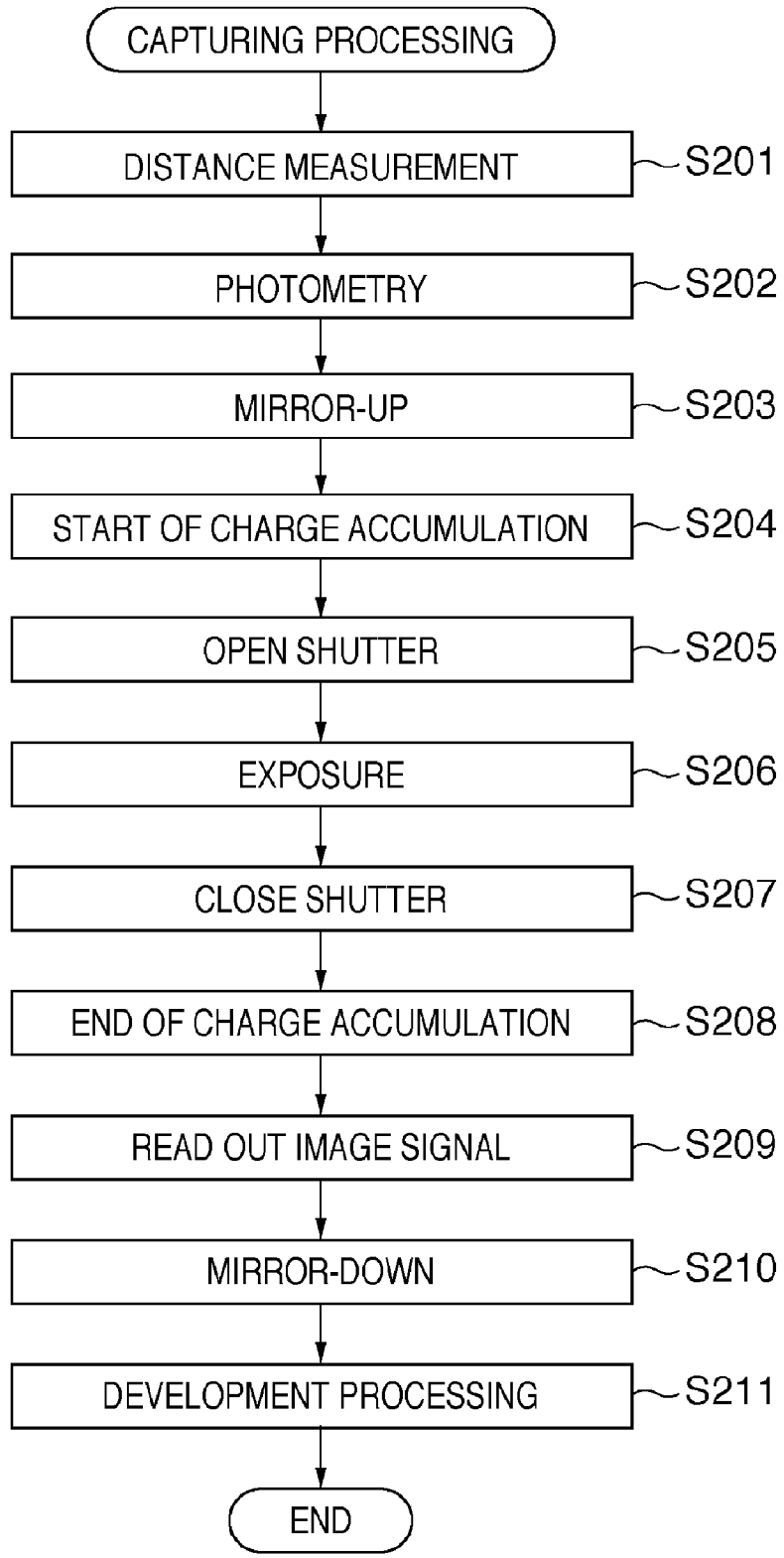
FIG. 2 is a flowchart showing image capture processing in the first embodiment.

Details of image capture processing will be explained with reference to a flowchart shown in FIG. 2.

When the user presses SW1 to designate the image capture process, the distance measurement control circuit 117 and AF control circuit 101a perform AF control in S201 to move the focusing lens to an in-focus position.

In S202, a photometry operation is done using the photometry control circuit 118, determining a shutter control value and aperture value to be controlled in accordance with a preset image capture mode. After the end of these operations, the microcomputer 127 instructs the mirror control circuit 116 in S203 on a so-called mirror-up operation to retract the quick return mirror 102 from the optical path of the image to be captured.

In S204, the image sensor 105 starts a charge accumulation.

In S205, the microcomputer 127 instructs the shutter control circuit 115 to open shutter 103 and perform exposure (S206).

In S207, the microcomputer 127 instructs the shutter control circuit 115 to close shutter 103. In S208, the image sensor 105 ends the charge accumulation.

In S209, the microcomputer 127 reads out an image signal from the image sensor 105, and temporarily stores, in the memory 113, image data processed by the A/D converter 106 and image processing circuit 107. Upon completion of reading out all image signals from the image sensor 105, the microcomputer 127 designates a so-called mirror-down operation in S210 to return the quick return mirror 102 to the optical path of the image sensing apparatus.

In S211, the microcomputer 127 generates image data by performing predetermined development processing for the image signal read out from the image sensor. The microcomputer 127 records the image data as an image file on the recording medium 200, and then ends the image capture processing.

In the image sensing apparatus of the first embodiment, the display unit 110 is usable as an electronic viewfinder. When a mode in which the display unit 110 is used as an electronic viewfinder is set with the operation switch 121, the microcomputer 127 instructs the mirror control circuit 116 to maintain the mirror-up state. Further, the microcomputer 127 instructs the shutter control circuit 115 to maintain the state in which the shutter 103 is open. In this state, image signals are sequentially read out from the image sensor 105. The image processing circuit 107 performs image processing for display on the display unit 110, thereby implementing a viewfinder function of displaying a through image on the display unit 110. Image capture processing operations in this state differ from the mirror control processes in S203 and S210 and the shutter control processes in S205 and S207. However, these processes are already well known and a description thereof will be omitted.

<Identification Data Registration Processing>

Figure 3:
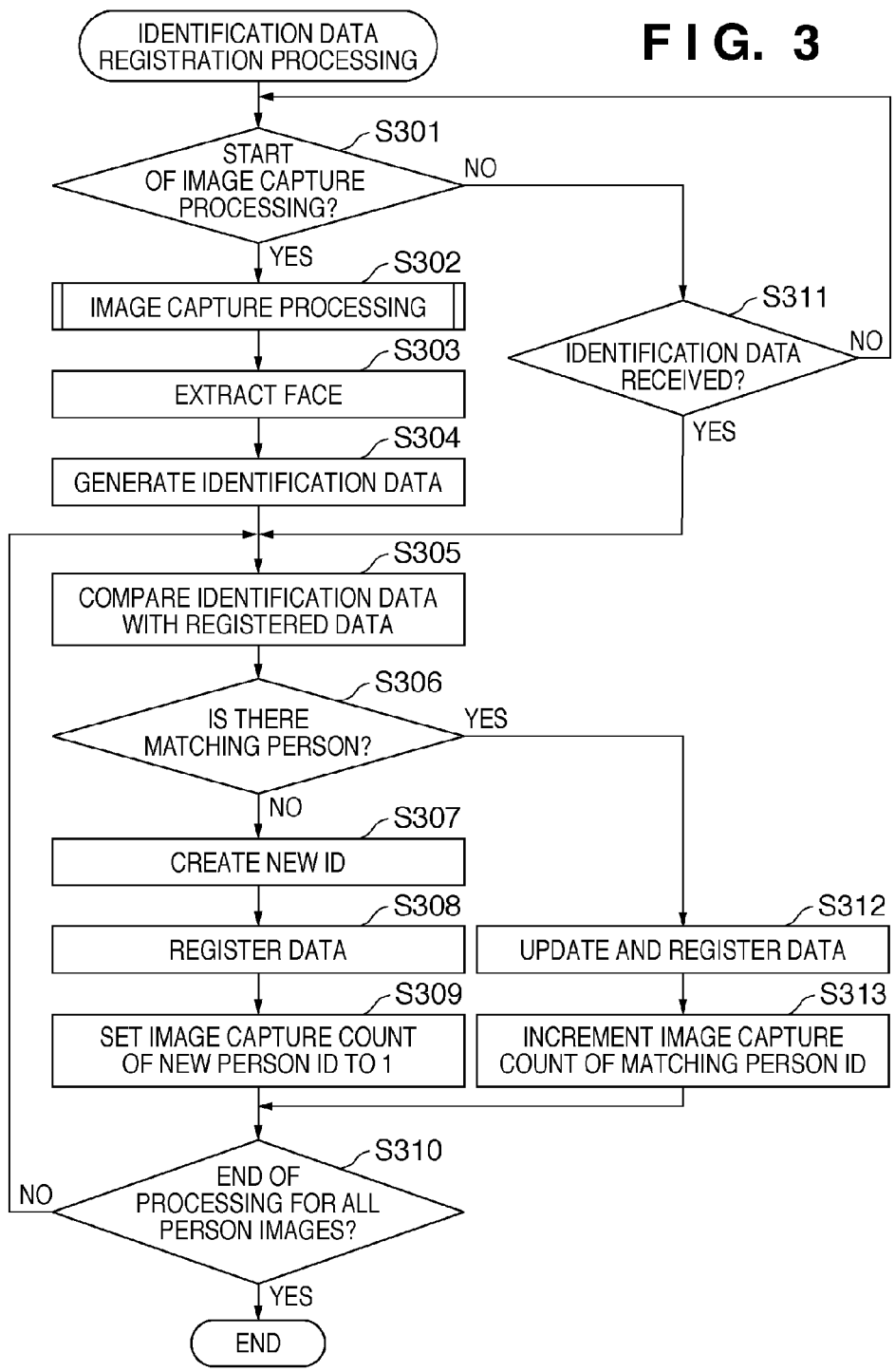
FIG. 3 is a flowchart showing identification data registration processing in the first embodiment.

Identification data registration processing will be explained with reference to a flowchart shown in FIG. 3.

In S301, the microcomputer 127 determines whether the user has pressed the release switch 120 to designate image capture processing. If the user has designated image capture processing, the process advances to S302 to execute image capture processing and record captured image data as an image file on the recording medium 200. In S303, the face recognition unit 126 extracts a face region from the captured image.

If the captured image data contains a person image, the face recognition unit 126 generates as many analysis data as extracted person images in S304.

In S305, data analyzed from the captured image data is compared with registered self-apparatus identification data recorded on the recording medium 200. If the analysis data does not match a person image in registered self-apparatus identification data (NO in S306), a person ID is newly generated as an identifier for managing identification data of a new person (S307). The analysis data is recorded as registered self-apparatus identification data on the recording medium 200 in association with the person ID (S308).

In the first embodiment, identification data may be recorded in the nonvolatile memory 119 or memory 113, instead of the recording medium 200.

In S309, the microcomputer 127 sets, to 1, an image capture count associated with the newly generated person ID. After registering identification data of the person image contained in the captured image data is ended, the process advances to S310. In S310, the microcomputer 127 determines whether the comparison processing and registration processing have been completed for all the extracted person images. If NO in S310, the process returns to S305 to repetitively execute a series of registration processes.

If there is registered self-apparatus identification data of a matching person image during the comparison process of S306, the process advances to S312. The microcomputer 127 updates the registered self-apparatus identification data of the matching existing person ID. As updating of registered self-apparatus identification data, it is also possible to additionally register analysis data as identification data for each person ID and associate a plurality of identification data. Alternatively, registered self-apparatus identification data may be updated by generating new identification data from existing registered self-apparatus identification data and analysis data or received identification data. This can enhance the reliability of registered self-apparatus identification data and further increase the identification rate of face recognition processing.

In S313, the microcomputer 127 increments by one an image capture count associated with the matching person ID. The process then advances to S310.

If the microcomputer 127 determines in S301 that the user has not designated image capture processing, the process advances to S311. The microcomputer 127 determines whether the self-apparatus has received identification data from another apparatus. If the self-apparatus has not received identification data from another apparatus, the process returns to S301. If the self-apparatus has received identification data from another apparatus, the process advances to S305. The microcomputer 127 compares the identification data with registered self-apparatus identification data recorded on the recording medium 200. Thereafter, the same processing as that for captured image data is done.

In the first embodiment, the timing when another apparatus transmits identification data is the time when it performs capturing processing and generates identification data. The self-apparatus receives the identification data generated by the other apparatus upon capturing. More specifically, the self-apparatus receives identification data generated by the other apparatus and compares it with registered self-apparatus identification data in the self-apparatus by the face recognition unit 126. At the same time, the self-apparatus uses the received identification data to count the image capture count of an object captured by the other apparatus. Identification data received from the other apparatus is recorded on the recording medium 200 and used as registered self-apparatus identification data.

In this manner, every time image capture processing is performed, a person appearing in captured image data is specified to update the image capture count. Also when identification data is received from another apparatus, the image capture count of a person specified from the identification data is updated.

<Database>

Figures 4, 5, 6:
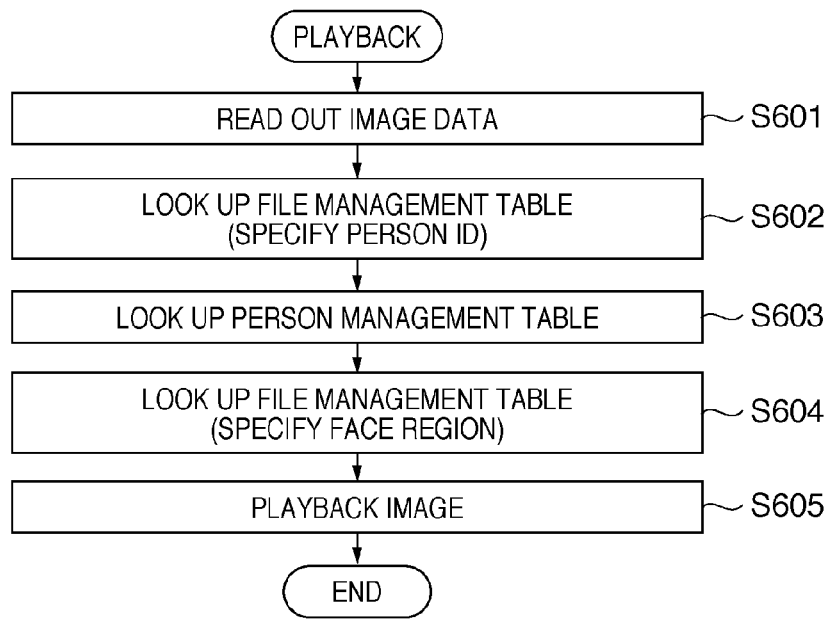
FIG. 4 is a table exemplifying the contents of a file management table in the first embodiment.
FIG. 5 is a table exemplifying the contents of a person ID management table in the first embodiment.
FIG. 6 is a flowchart showing playback processing in the first embodiment.

FIG. 4 exemplifies a data structure recorded on the recording medium 200 as a database representing the identification result of an object analyzed by the face recognition unit 126 in an image data file recorded upon image capture processing. This database will be called a file management table.

In FIG. 4, a "file name" is the file name of an image file recorded on the recording medium 200 and is assigned according to a predetermined naming convention upon image capture. A "person ID" is a person ID for specifying a person captured in an image file. As shown in FIG. 3, the person ID is a unique ID for specifying a person whose image is processed by the face recognition unit 126. A "number of persons" is the number of person images extracted by the face recognition unit 126. A "face region" is an X-Y coordinate point indicating the position of a face extracted by the face recognition unit 126. For each person ID, the coordinate position is managed. This database is updated every time a captured image file is created.

Note that contents managed in the file management table are not limited to those above.

FIG. 5 exemplifies a data structure for recording predetermined data managed for each person ID on the recording medium 200. This data structure will be called a person ID management table.

In FIG. 5, the person ID is a unique ID for specifying a person. The image capture count is the number of image data in which data analyzed by the face recognition unit 126 from image data captured by the self-apparatus match registered self-apparatus identification data of each person ID, as described with reference to FIG. 3. The image capture count is that of each object. The registered self-apparatus identification data also contains identification data received from another apparatus.

Note that contents managed in the person ID management table are not limited to those above.

<Playback Processing>

The process of playing back an image file recorded on the recording medium 200 will be explained with reference to a flowchart shown in FIG. 6.

When the user manipulates the playback key of the operation switch 121 to designate playback, an image file is read out from the recording medium 200 into memory 113 in S601 of FIG. 6.

The process advances to S602, and the microcomputer 127 looks up the file management table to specify the person ID of an object captured in the read image file. The microcomputer 127 looks up the person ID management table to grasp the image capture count of each person ID specified in S602 (S603).

In S604, the microcomputer 127 looks up the file management table to refer to a face region for each person ID and grasp its position. In S605, the image processing circuit 107 processes the read image file to superimpose and display the image capture count near the face region of each object. The processed data is transferred to the image display memory 112 and displayed on the display unit 110. Near the face region, the display of the image capture count may or may not overlap the face region.

<Display Window>

Figure 7:
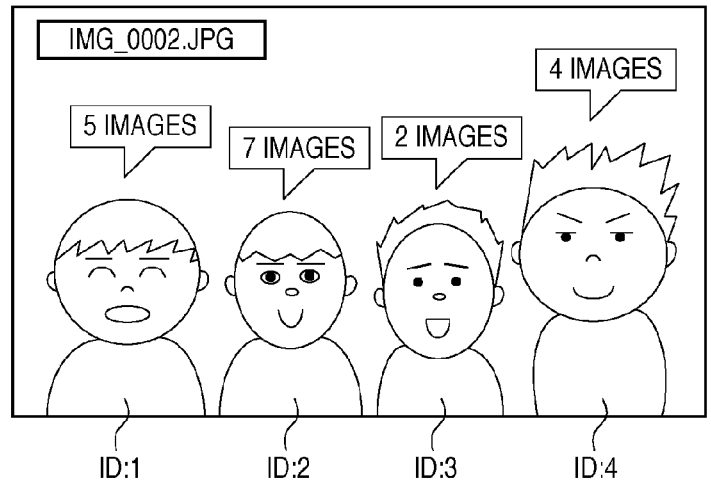
FIG. 7 is a view exemplifying a playback window in the first embodiment.

FIG. 7 exemplifies a display window when an image is played back. The window represents four persons, and an image file "IMG_0002.JPG" is played back. A numeral near each face indicates the image capture count of each person. Persons with person IDs of 1, 2, 3, and 4 from the left person in the window are captured.

In this fashion, when an image file is played back, the image capture count of each person captured in the image file can be easily grasped. Note that the displayed image capture count contains not only the image capture count of an object by the self-apparatus but also that of the object by another apparatus.

Figure 8:
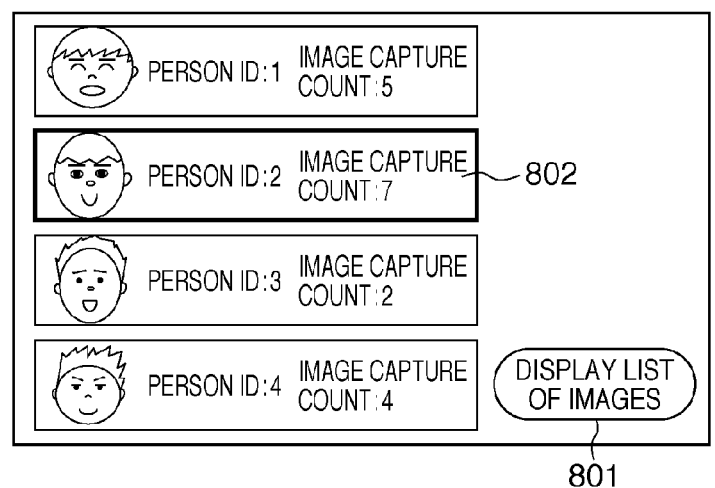
FIG. 8 is a view exemplifying display of a list of registered persons in the first embodiment.

FIG. 8 exemplifies a list of the contents of the person ID management table displayed on the display unit 110.

As shown in FIG. 8, the display unit 110 displays a list of the person ID, corresponding face image, and image capture count. As the face image, for example, image data of a face region extracted by the face recognition unit 126 suffices to be recorded as a thumbnail image together with identification data in association with a person ID in identification data registration processing shown in FIG. 3. The thumbnail image of a person captured by another apparatus suffices to be received simultaneously when receiving identification data from the other apparatus.

The window prepares an icon used to designate display of an image list by the user. The user manipulates a selection frame 802 from the list display to select a desired person. Then, the user manipulates an "image list display" icon 801 at the lower right portion of the window. In response to this, image files containing the target person image are read out from the recording medium 200 to display a list.

Figure 9:
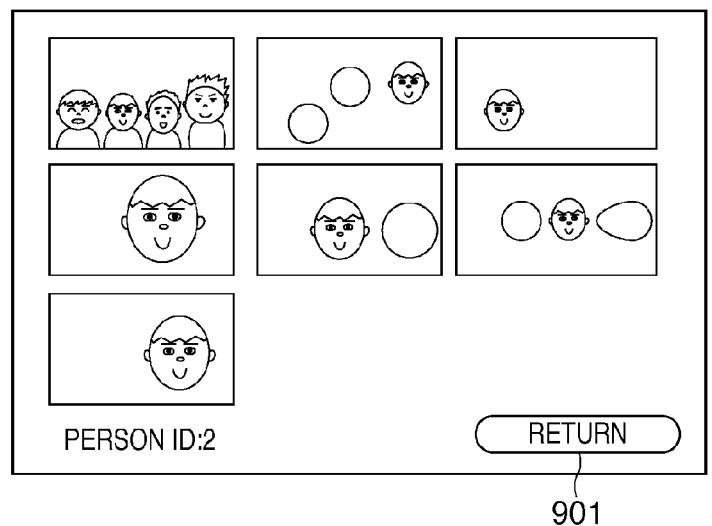
FIG. 9 is a view exemplifying display of a playback list in the first embodiment.

FIG. 9 exemplifies display of a list of image files containing images of a selected person.

The list display of image capture statuses for each person allow the user to easily grasp whether the image capture count of each person is low or high. The displayed image capture status contains both an image capture count by the self-apparatus and that by another apparatus. Even when one user takes pictures at an event with a plurality of cameras while changing cameras, or even when a plurality of users take pictures, captured images can be shared between cameras. The user can easily grasp the image capture status in order to equally capture participants in the event. The window prepares a "return" icon 901 used by the user to designate return to a window before manipulating the image list display icon 801.

In the list display example shown in FIG. 8, images are listed in ascending order of the person ID. Instead, images may be sorted based on image capture information. For example, images may be sorted based on information representing whether the image capture count is high or low. From this, the user can more easily grasp the image capture status of a person who has not been captured.

In the first embodiment, it is configured to receive identification data of an object captured by another apparatus. However, the present invention is not limited to this, and it is also possible to receive the image of a face region extracted by another apparatus and generate identification data of the other apparatus by the face recognition unit 126.

The first embodiment has referred to only an arrangement in which identification data is received from another apparatus. Needless to say, the self-apparatus may transmit identification data to another apparatus.

According to the first embodiment, identification data which is generated by analyzing image data captured by the self-apparatus in order to specify a person is compared with person identification data received from another apparatus. Then, the image capture status is displayed, including an uncaptured object and the image capture count for each object. Even when one user takes pictures at an event while changing a plurality of cameras, or even when a plurality of users take pictures, the image capture status can be shared between a plurality of cameras. The user can easily grasp a status for equally capturing participants in the event.

Second Embodiment

Next, the second embodiment will be described.

The arrangement of an image sensing apparatus in the second embodiment is the same as that described in the first embodiment with reference to FIG. 1, and a description thereof will not be repeated.

The second embodiment will explain an image sensing apparatus capable of notifying the user of the image capture status of an object while using the electronic viewfinder function.

In the second embodiment, registration processing of identification data for identifying a person is executed by the same procedures as those in the first embodiment.

<Viewfinder Display Processing>

A method of displaying the image capture status of an object on the viewfinder to notify the user of it will be explained with reference to the flowchart of FIG. 10.

Figure 10:
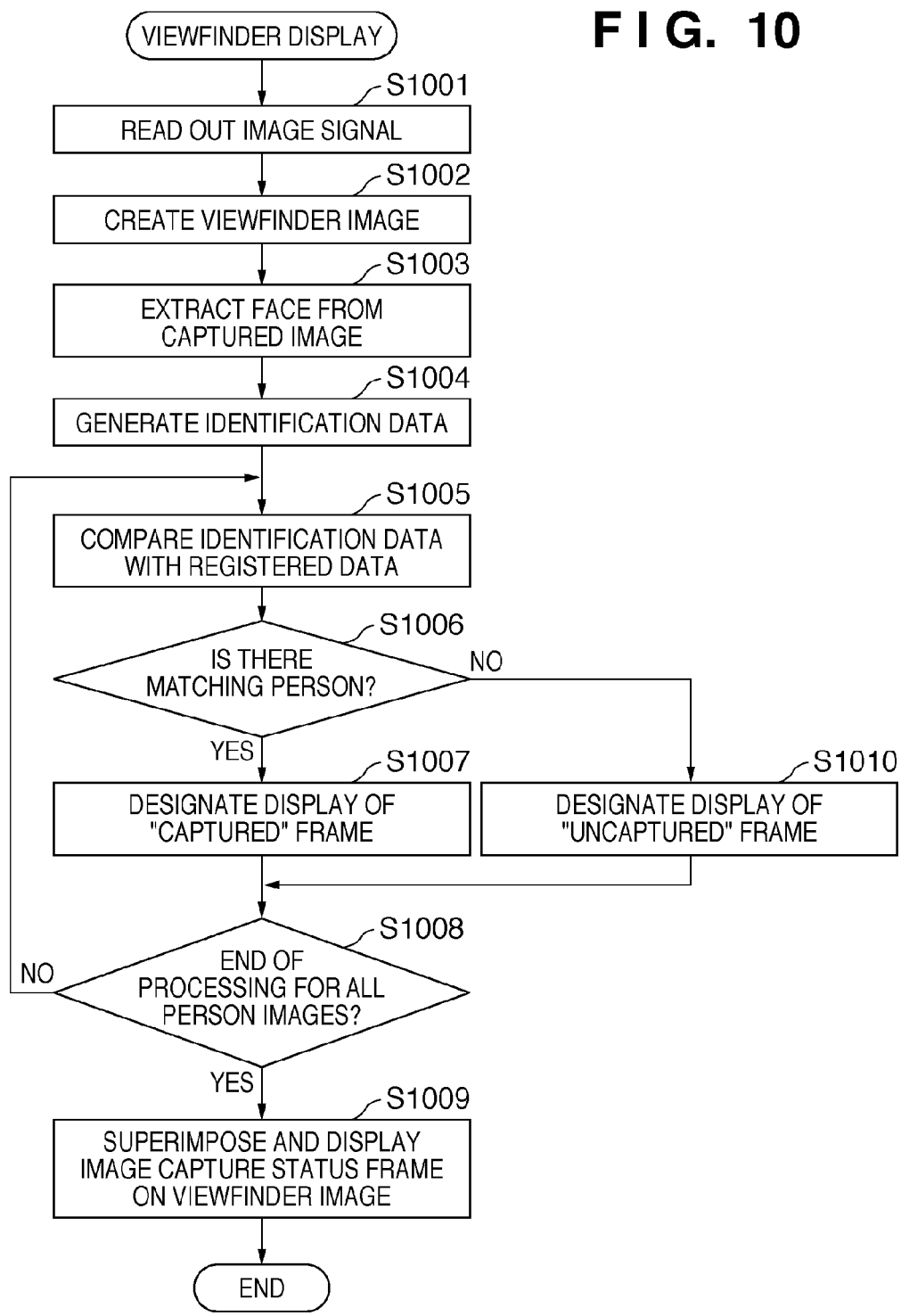
FIG. 10 is a flowchart showing viewfinder display processing in the second embodiment.

In S1001 of FIG. 10, a microcomputer 127 reads out an image signal from an image sensor 105. An A/D converter 106 and image processing circuit 107 process the image signal. Through image data to be displayed on the electronic viewfinder is temporarily stored in a memory 113 (S1002).

In S1003, a face recognition unit 126 extracts a face region from the image data temporarily stored in the memory 113.

In S1004, if the captured image data contains a person image, the face recognition unit 126 generates as many analysis data as extracted person images. In S1005, the analysis data is compared with registered self-apparatus identification data recorded on a recording medium 200. The registered self-apparatus identification data also contains identification data received from another apparatus, similar to the first embodiment.

In S1006, the microcomputer 127 determines whether the analysis data matches registered self-apparatus identification data. If the analysis data matches registered self-apparatus identification data, the process advances to S1007. In S1007, the microcomputer 127 designates to display, in the face region of a matching person in the image data, an index representing that the person has been captured.

If the microcomputer 127 determines in S1006 that the analysis data does not match registered self-apparatus identification data, the process advances to S1010. The microcomputer 127 designates to display, in the face region of the target person, an index representing that the person has not been captured.

After the end of recognizing the image capture status of the person image extracted from the through image data, the process advances to S1008. The microcomputer 127 determines whether the image capture status of all the person images extracted in S1003 have been recognized. If NO in S1008, the process returns to S1005 to repetitively execute a series of recognition processes. If the image capture status of all the person images have been recognized, the process advances to S1009. The image processing circuit 107 processes data to superimpose and display, on a through image, an index designated for each object in S1007 or S1010. The processed data is transferred to an image display memory 112 and displayed on a display unit 110 under the control of a display control circuit 109.

The process of superimposing an index is repetitively executed in synchronization with the reception of identification data from another apparatus while the display unit 110 displays a through image.

Figure 11A:
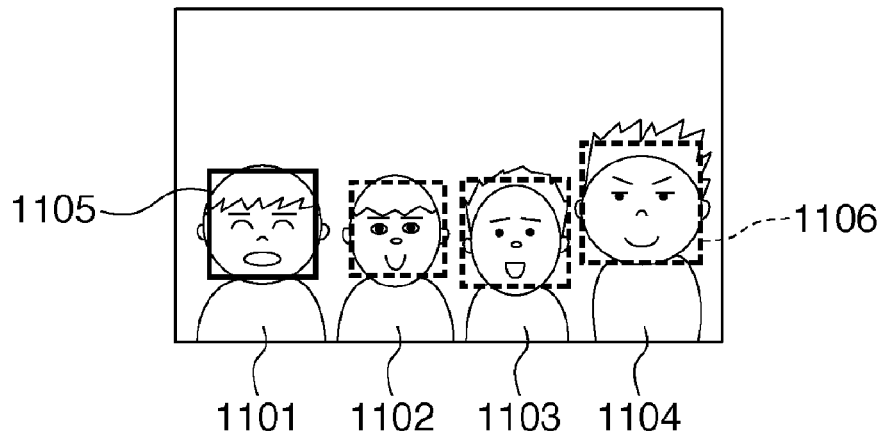
FIGS. 11A to 11C are views exemplifying viewfinder display windows in the second embodiment.
Figure 11B:
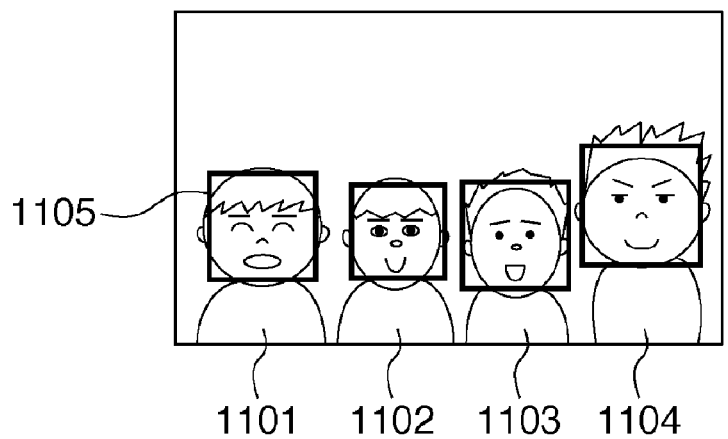
Figure 11C:
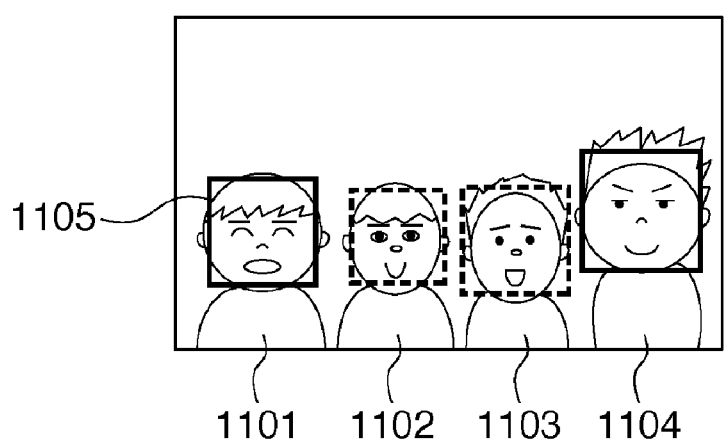

FIGS. 11A to 11C exemplify windows when the display unit 110 is used as an electronic viewfinder. In these examples, the image capture status of each object is superimposed and displayed on a through image.

In the second embodiment, indices (frames) different in the display form are superimposed and displayed in respective face regions.

In FIG. 11A, an uncaptured object exists in the viewfinder frame. In FIG. 11A, a person 1101 is an object who has already been captured. Persons 1102, 1103, and 1104 are objects who have not been captured yet.

In FIG. 11A, frames different in color are superimposed in face regions in a through image. For example, a dark-colored frame is superimposed in the face region of an object determined to have been captured. A light-colored frame is superimposed in the face region of an object determined not to have been captured. Captured and uncaptured objects are displayed discriminately.

In FIG. 11B, an uncaptured object in FIG. 11A exists in the viewfinder frame. FIG. 11B shows a through image after capturing by the self-apparatus. While the through image is displayed, the processes shown in FIG. 10 are executed sequentially. When the self-apparatus executes image capturing, light-colored frames are superimposed and displayed to represent that all objects have been captured, as shown in FIG. 11B.

In FIG. 11C, an uncaptured object in FIG. 11A exists in the viewfinder frame. FIG. 11C shows a through image after another apparatus captures an image containing the person 1104. When another apparatus captures an image containing the person 1104, identification data of the person 1104 is transmitted from the other apparatus and received by the self-apparatus. While the through image is displayed, the processes shown in FIG. 10 are executed sequentially. The image of the person 1104 in the through image in the self-apparatus changes to a display in which a dark-colored frame is superimposed to represent that the person 1104 has been captured.

In the second embodiment, indices indicating whether each object has been captured are superimposed and displayed as frames in different color in face regions. However, the present invention is not limited to this form. For example, the color, index, and display form are arbitrary as long as uncaptured and captured objects can be discriminated and identified. For example, an index may be superimposed and displayed on a through image for only an uncaptured or captured object.

Different indices may be displayed for an object captured by only the self-apparatus and one captured by only another apparatus. The image capture status of each object may be displayed outside the frame of a through image so that the user can recognize the image capture status.

Figure 12:
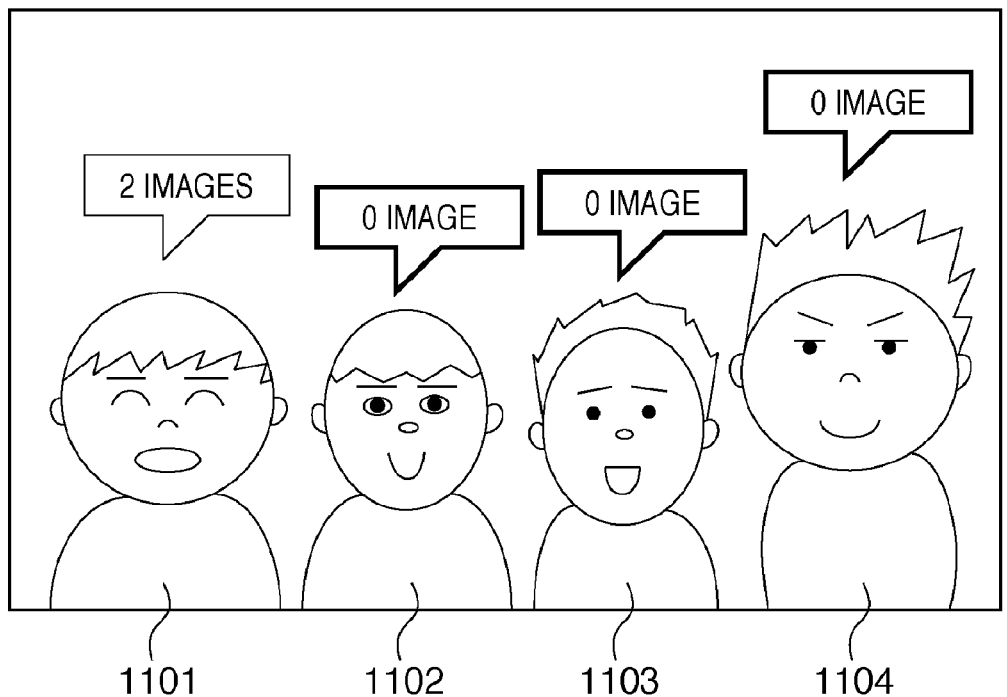
FIG. 12 is a view showing another example of the viewfinder display window in the second embodiment.

An index indicating the image capture count for each object may be superimposed and displayed on a through image, as shown in FIG. 12. In FIG. 12, an index indicating the image capture count of an uncaptured object and an index indicating that of a captured object are displayed identifiably in different colors.

The second embodiment has only referred to an arrangement in which identification data is received from another apparatus. The self-apparatus may also transmit identification data to another apparatus.

According to the second embodiment, identification data which is generated by analyzing image data captured by the self-apparatus in order to specify a person is compared with person identification data received from another apparatus. Then, the image capture status is displayed on the viewfinder, including an uncaptured object and the image capture count of each object. Even when one user takes pictures at an event while changing a plurality of cameras, or even when a plurality of users take pictures, the image capture status can be shared between a plurality of cameras. The user can easily grasp the status for participants that have been equally captured in the event.

Every time another apparatus takes a picture, information of the object captured by the other apparatus is updated even while the user sees the viewfinder and executes framing of an image. Since the image capture status can be shared between cameras, the user can sequentially grasp information for participants that have been equally captured in an event.

Third Embodiment

The third embodiment will be described.

The arrangement of an image sensing apparatus in the third embodiment is the same as that described in the first embodiment with reference to FIG. 1, and a description thereof will not be repeated.

The third embodiment will explain a method of transmitting/receiving an image file to/from another apparatus based on registered self-apparatus identification data and identification data received from the other apparatus.

<Identification Data Registration Processing>

Identification data registration processing in the third embodiment will be explained with reference to flowcharts shown in FIGS. 13A and 13B. Note that image capture processing is the same as the sequence described in the first embodiment with reference to FIG. 2, and a description thereof will not be repeated.

Figure 13A:
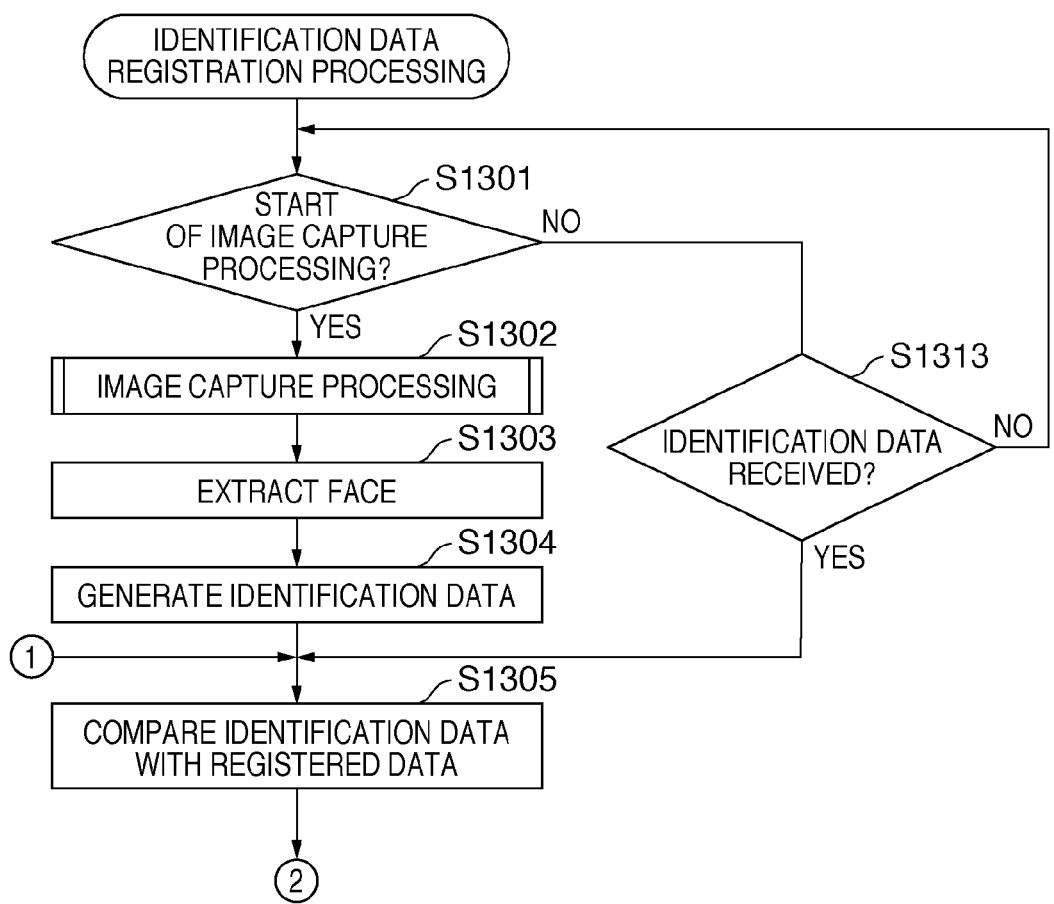
FIGS. 13A and 13B are flowcharts showing identification data registration processing in the third embodiment.
Figure 13B:
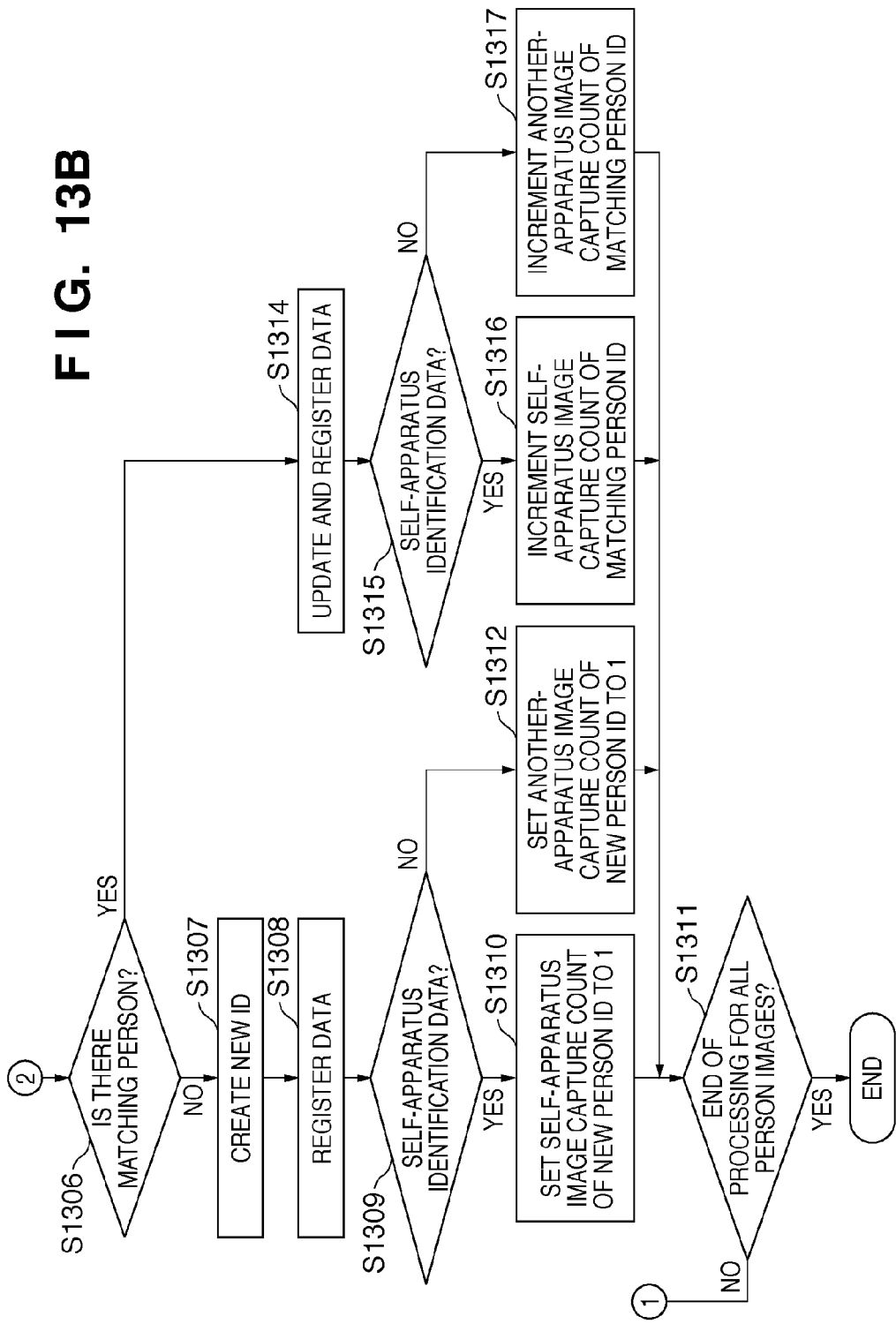

In S1301 of FIG. 13A, a microcomputer 127 determines whether the user has pressed a release switch 120 to designate image capture processing. If the user has designated image capture processing, the process advances to S1302 to execute the image capture process and record captured image data as an image file on a recording medium 200.

In S1303, a face recognition unit 126 extracts a face region from the captured image data. If the captured image data contains a person image, the face recognition unit 126 generates as many analysis data as extracted person images in S1304. In S1305, data analyzed from the captured image data is compared with registered self-apparatus identification data recorded on the recording medium 200. In S1306 of FIG. 13B, if the analysis data does not match a person image in registered self-apparatus identification data (NO in S1306), the face recognition unit 126 generates a person ID as an identifier for managing identification data of a new person (S1307). The analysis data is recorded as registered self-apparatus identification data on the recording medium 200 in association with the person ID (S1308).

In the third embodiment, identification data is recorded on the recording medium 200, but may be stored in a nonvolatile memory 119 or memory 113.

In S1309, the microcomputer 127 determines whether the registered identification data is identification data generated by the self-apparatus upon image capture or one received from another apparatus. If the registered identification data is identification data generated by the self-apparatus, the process advances to S1310 to set, to 1, an image capture count associated with the newly generated person ID in the self-apparatus. If the registered identification data is identification data received from another apparatus, the process advances to S1312 to set, to 1, an image capture count associated with the newly generated person ID in the other apparatus. After the end of registering identification data, the process advances to S1311. The microcomputer 127 determines whether the registration processing has been completed for all the person images extracted in S1303. If NO in S1310, the process returns to S1305 to repetitively execute a series of processes.

If there is registered self-apparatus identification data of a matching person in S1306, the process advances to S1314. The microcomputer 127 updates the registered self-apparatus identification data of the matching existing person ID.

For updating of registered self-apparatus identification data, it is also possible to additionally register analysis data as identification data for each person ID and associate a plurality of identification data. Alternatively, registered self-apparatus identification data may be updated by generating new identification data from existing registered self-apparatus identification data and analysis data or received identification data. This can enhance the reliability of registered self-apparatus identification data and further increase the identification rate for face recognition processing.

In S1315, the microcomputer 127 determines whether the updated identification data is identification data generated by the self-apparatus upon image capture or one received from another apparatus. If the updated identification data is identification data generated by the self-apparatus, the process advances to S1316. The microcomputer 127 increments by one an image capture count associated with the matching person ID. The process then advances to S1311.

If the microcomputer 127 determines in S1315 that the updated identification data is identification data received from another apparatus, the process advances to S1317. The microcomputer 127 increments by one an image capture count associated with the matching person ID in the other apparatus. After updating the identification data, the process advances to S1311. The microcomputer 127 determines whether the update process and registration process have been completed for all the person images extracted in S1304. If NO in S1311, the process returns to S1305 to repeat a series of processes.

If the microcomputer 127 determines in S1301 that the user has not designated the image capture process, the process advances to S1313. The microcomputer 127 determines whether the self-apparatus has received identification data from another apparatus. If the self-apparatus has not received identification data from another apparatus, the process returns to S1301. If the self-apparatus has received identification data from another apparatus, the process advances to S1305 to compare the identification data with registered self-apparatus identification data recorded on the recording medium 200. Then, the same process as that for captured image data is carried out.

In the third embodiment, the timing when another apparatus transmits identification data is the time when it performs image capture processing and generates identification data. The self-apparatus receives the identification data generated by the other apparatus upon image capture. More specifically, the self-apparatus receives identification data generated by the other apparatus and uses it for comparison with registered self-apparatus identification data in the self-apparatus by the face recognition unit 126. At the same time, the self-apparatus uses the received identification data to increment the image capture count of an object captured by the other apparatus.

As described above, every time an image capture process is performed, a person appearing in captured image data is specified to update the image capture count. Also when identification data is received from another apparatus, the image capture count of a person specified from the identification data is updated. Then it is determined as to whether the image capture was executed by the self-apparatus or another apparatus in order to increment the image capture count.

<Database>

FIG. 14 exemplifies the data structure of a person ID management table managed for each person ID in the third embodiment.

In FIG. 14, the person ID is a unique ID for specifying a person. The image capture count by the self-apparatus is the number of image data at which data analyzed by the face recognition unit 126 from image data captured by the self-apparatus match registered self-apparatus identification data of each person ID, as described with reference to FIGS. 13A and 13B. The image capture count by the self-apparatus is that of an object captured by the self-apparatus. The image capture count by another apparatus is the number of image data at which identification data received from another apparatus match registered self-apparatus identification data of each person ID. The image capture count by another apparatus is that of an object captured by another apparatus.

<Display Window>

FIG. 15 exemplifies a list of the contents of the person ID management table in FIG. 14 displayed on a display unit 110. As shown in FIG. 15, the display unit 110 displays a list of the person ID, corresponding face image, image capture count by the self-apparatus, image capture count by another apparatus, and total image capture count by the self-apparatus and another apparatus. For the face image, for example, image data of a face region extracted by the face recognition unit 126 suffices to be recorded as a thumbnail image together with identification data in association with a person ID in the identification data registration process shown in FIGS. 13A and 13B. The thumbnail image of a person captured by another apparatus suffices to be received simultaneously when receiving identification data from the other apparatus.

The window shown in FIG. 15 prepares icons for acquiring an image file from another apparatus. More specifically, an "uncaptured images" icon 1501 is used to designate acquisition of images capturing an object not captured by the self-apparatus. An "all images" icon 1502 is used to designate acquisition of all image files captured by another apparatus. A "selected person's images" 1503 is used to designate acquisition of image files corresponding to a specific person ID selected by a selection frame 1504. When the user manipulates a desired icon, the microcomputer 127 transmits a request to another apparatus to acquire a corresponding image file in accordance with the manipulation instruction. The microcomputer 127 receives the image file transmitted from the other apparatus, and records it on the recording medium 200.

The third embodiment has referred to only an arrangement in which identification data is received from another apparatus. The self-apparatus may also transmit identification data to another apparatus.

According to the third embodiment, identification data which is generated by analyzing image data captured by the self-apparatus in order to specify a person, is compared with person identification data received from another apparatus. Then, the image capture status is displayed, including an uncaptured object and the image capture count of each object. Even when one user takes pictures at an event while changing a plurality of cameras, or even when a plurality of users take pictures, the image capture status can be shared between a plurality of cameras. The user can easily grasp the image capture status of each camera and the status of equally captured participants in the event.

Every time another apparatus takes a picture, information of the object captured by the other apparatus is updated even as the user sees the viewfinder and executes framing of an image. Since the image capture status can be shared between cameras, the user can sequentially grasp information for equally captured participants in an event.

By using information of the image capture status shared between a plurality of cameras, a target file for transmitting/receiving images to/from another apparatus can be easily selected and transmitted/received.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-022959, filed Feb. 3, 2009 which is hereby incorporated by reference herein in its entirety.

What is claimed is:

1. An image sensing apparatus that is capable of communicating with another image sensing apparatus, comprising:
an image sensing unit configured to sense an object and generate image data;
an identification data generation unit configured to generate, from the image data, identification data for identifying a feature of the object;
a storage unit configured to store the identification data;
a display unit configured to display the image data;
a communication unit configured to receive identification data for identifying a feature of an object, wherein the object is captured by the other image sensing apparatus while the image sensing apparatus is communicating with the other image sensing apparatus;
a determination unit configured to determine the image capture status of each object based on the identification data received by said communication unit; and
a control unit configured to control said display unit to identifiably display the image capture status of each object based on the determination by said determination unit.

2. The apparatus according to claim 1, further comprising a comparison unit configured to compare the identification data stored in said storage unit with the identification data received from the other image sensing apparatus,
wherein said determination unit determines the image capture status of each object based on a comparison result by said comparison unit.

3. The apparatus according to claim 1, wherein
said determination unit determines whether the image data contains an object which has not been captured yet, and
when said determination unit determines that the image data contains an object which has not been captured yet, said control unit controls said display unit to display the object identifiably from another object.

4. The apparatus according to claim 1, further comprising a counting unit configured to count, based on the identification data received by said communication unit, an image capture count of each object identified by the identification data,
wherein said control unit controls to display the image capture count of each object.

5. The apparatus according to claim 1, wherein said storage unit stores identification data which is received by said communication unit to identify a feature of an object captured by the other image sensing apparatus.

6. The apparatus according to claim 1, wherein said control unit performs control to update display of an object by said display unit in synchronization with reception of identification data from the other image sensing apparatus.

7. The apparatus according to claim 1, wherein said communication unit can receive identification data from a plurality of other image sensing apparatuses, wherein said apparatus further comprises a counting unit configured to count, for each image sensing apparatus, based on the identification data received by said communication unit, an image capture count of each object identified by the identification data, and wherein said control unit performs control to display the image capture count of each object for each image sensing apparatus.

8. The apparatus according to claim 1, wherein
said display unit includes an electronic viewfinder which displays image data sequentially output from said image sensing unit while updating the image data, and
said identification data generation unit generates identification data from the sequentially updated image data.

9. A method of controlling an image sensing apparatus that is capable of communicating with another image sensing apparatus, the image sensing apparatus including an image sensing unit configured to sense an object and generate image data, an identification data generation unit configured to generate, from the image data, identification data for identifying a feature of the object, a storage unit configured to store the identification data, and a display unit configured to display the image data, the method comprising the steps of:
receiving, via a communication unit, identification data for identifying a feature of an object, the object being captured by the other image sensing apparatus while the image sensing apparatus is communicating with the other image sensing apparatus;

determining the image capture status of each object based on the identification data received in the receiving step; and controlling the display unit to identifiably display the image capture status of each object based on the determination in the determining step.

10. A non-transitory computer-readable storage medium storing a program which causes a computer to execute a control method defined in claim 9.

* * * * *